(12) United States Patent
Rawls et al.

(10) Patent No.: US 10,561,763 B2
(45) Date of Patent: Feb. 18, 2020

(54) OXYGEN GENERATING BIOMATERIAL

(71) Applicants: Henry Ralph Rawls, San Antonio, TX (US); Ahsan Ullah Khan, New York, NY (US)

(72) Inventors: Henry Ralph Rawls, San Antonio, TX (US); Ahsan Ullah Khan, New York, NY (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/678,281

(22) Filed: Aug. 16, 2017

(65) Prior Publication Data

US 2017/0368228 A1    Dec. 28, 2017

Related U.S. Application Data

(62) Division of application No. 15/034,668, filed as application No. PCT/US2014/064440 on Nov. 6, 2014, now Pat. No. 9,750,849.

(60) Provisional application No. 61/900,915, filed on Nov. 6, 2013.

(51) Int. Cl.

| | |
|---|---|
| *A61L 27/54* | (2006.01) |
| *A61L 27/52* | (2006.01) |
| *A61L 15/44* | (2006.01) |
| *A61C 8/02* | (2006.01) |
| *A61F 13/02* | (2006.01) |

(Continued)

(52) U.S. Cl.
CPC ............ *A61L 27/54* (2013.01); *A61C 8/0006* (2013.01); *A61F 13/0206* (2013.01); *A61K 31/01* (2013.01); *A61K 31/357* (2013.01); *A61L 15/44* (2013.01); *A61L 27/52* (2013.01); *A61L 2300/20* (2013.01)

(58) Field of Classification Search
None
See application file for complete search history.

(56) References Cited

U.S. PATENT DOCUMENTS

2009/0292357 A1 * 11/2009 McCoy ................ A01N 61/00
                                                                 623/6.56

FOREIGN PATENT DOCUMENTS

| WO | 02087644 | * 11/2002 |
| WO | 2008000198 | * 1/2008 |
| WO | WO/08/000198 | 1/2008 |

OTHER PUBLICATIONS

Stahl et al., Carcinogenesis (1997) 18, 1, pp. 89-92.*

(Continued)

*Primary Examiner* — Karl J Puttlitz
(74) *Attorney, Agent, or Firm* — Norton Rose Fulbright US LLP

(57) ABSTRACT

Certain embodiments include materials that carry oxygen and emit molecular oxygen upon heating. The approach reported here uses thermal decomposition of organic endoperoxide compounds to produce singlet oxygen. In certain aspects the oxygen carrier comprises an organic compound either alone or contained in a polymeric carrier or other carrier material that is used to form a coating, layer, or bulk substance that can be a solid, a gel or a fluid. The oxygen-carrier is most conveniently prepared by oxidation of a precursor compound, the structure of which determines its thermal stability and thus how rapidly oxygen is released at any given temperature.

6 Claims, 5 Drawing Sheets

(51) Int. Cl.
*A61K 31/01* (2006.01)
*A61K 31/357* (2006.01)

(56) References Cited

OTHER PUBLICATIONS

Ninan et al., Carbohydr Polym. Oct. 15, 2013;98(1):877-85 (Year: 2013).*
Abdi et al. An enzyme-modulated oxygen-producing micro-system for regenerative therapeutics. International Journal of Pharmaceutics. May 2011, vol. 409, No. 1-2: 203-205.
Bloch et al. Photosynthetic Oxygen Generator for Bioartificial Pancreas, Tissue Engineering 12(2), 2006, pp. 337-344.
Carlsson et al., Photooxidation of Unsaturated Oils: Effects of Singlet Oxygen Quenchers, Journal of the American Oil Chemists' Society, vol. 53, 1976, pp. 656-660.
Davis, 2007. How might we achieve oxygen balance in wounds? International Wound Journal, vol. 4, Supp. 3, No. 3, pp. 18-24, 2007.
Galway et al. Thermal decomposition of sodium carbonate perhydrate in the Solid State. The Journal of Physical Chemistry, vol. 83, No. 14, 1979, pp. 1810-1815.
Guo and DiPietro, Factors Affecting Wound Healing, J Dent Res 89(3): 2010.
Harrison et al. Oxygen Producing Biomaterials for Tissue Regeneration. Biomaterials, vol. 28, No. 31, 2007, pp. 4628-4634.
International Preliminary Report on Patentability in International Application No. PCT/US2914/064440 dated May 19, 2016.
International Search Report and Written Opinion in International Application No. PCT/US2914/064440 dated Feb. 13, 2015.
Luo, Kinetics of Singlet Oxygen Release from Endoperoxides of 2-Pyridone derivative, Bachelor of Science Dissertation, Worcester Polytechnic Institute, May 3, 2011.
Oh et al. Oxygen generating scaffolds for enhancing engineered tissue survival. J Biomaterials. vol. 30, No. 5, 2009, pp. 757-762.
Ouchi et al. "Kinetic study of the quenching reaction of singlet oxygen by carotenoids and food extracts in solution. Development of a singlet oxygen absorption capacity (SOAC) assay method." J. Agric. Food Chem., vol. 58, 2010, pp. 9967-9978.
Pierlot, et al., "Naphthalene Endoperoxides as Generators of Singlet Oxygen in Biological Media." Methods in Enzymology. 319: 3-20, 2000.
Posavec D (Oct. 2010). Adjustment of the decay kinetics of photogenerated endoperoxides embedded in various carrier materials aiming at medical application. PhD Dissertation, University of Regensburg, Federal Republic of Germany.
Rawls and Santen, A Possible Role for Singlet Oxygen in the Initiation of Fatty Acid Autooxidation. J Am Oil Chem Soc (1970) 47: 121.
Roe et al. Topical Dissolved Oxygen Penetrates Skin: Model and Method. Journal of Surgical Research, Mar. 2010 vol. 159, Issue 1, pp. e29-e36.
Schaap et al. Polymer-based Sensitizers for photooxidations. II. Journal of the American Chemical Society, 97(13): 3741-3745.
Smith et al., "Locally enhanced angiogenesis promotes transplanted cell survival." Tissue Engineering 2004, vol. 10, pp. 63-71.
Stahl, et al., "Biological Activities of Natural and Synthetic Carotenoids: Induction of Gap Junctional Communication and Single Oxygen Quenching." Cardinogenesis. 18(1):89-92, 1997.
Steinbeck et al. Intracellular Singlet oxygen generation by phagocytosing neutrophils in response to particles coated with a chemical trap. Journal of Biological Chemistry, 1992, vol. 267, No. 19, pp. 13425-13433.
Young, et al., A Novel Absorptive Dressing Containing Oxygen Significantly Increases Healing Rate in Porcine Dermal Wounds Presented at the semi-annual SAWC Fall Conference, Las Vegas NV; Oct. 2014.
Zellner S, Manabat R, and Roe DF. A dissolved oxygen dressing: A pilot study in an ischemic skin flap model. Journal of International Medical Research published online Nov. 12, 2014.
Zhang, et al., "Oxygen delivery augmented bone formation from transplanted bone marrow." Frontiers in Bioengineering and Biotechnology (URL=http://www.frontiersin.org, DOI=10.3389/conf.FBIOE.2016.01.03013, ISSN=2296-4185).

* cited by examiner

OXYGEN GENERATING BIOMATERIAL

This application is a divisional application from U.S. application Ser. No. 15/034,668 filed May. 5, 2016 which is a national phase application under 35 U.S.C. § 371 from International Application No. PCT/US2014/064440 filed on Nov. 6, 2014, which claims priority to U.S. Application No. 61/900,915 filed on Nov. 6, 2013. The entire contents of each of the above-referenced disclosures are specifically incorporated herein by reference without disclaimer.

BACKGROUND

Oxygen is often employed to heal wounds (e.g., ulcers, abrasions, cuts, sores, etc.). Topical oxygen therapy calls for applying oxygen directly to an open wound. The oxygen dissolves in tissue fluids and improves the oxygen content of the intercellular fluids. Injuries and disorders which may be treated with topical oxygen include osteomylelitis, tendon and cartilage repair, sprains, fractures, burns and scalds, necrotizing fasciitis, pyoderma gangrenosum, refractory ulcers, diabetic foot ulcers and decubitus ulcers (bed sores) as well as cuts, abrasions, and surgically induced wounds or incisions.

Certain wounds and injuries can be treated using tissue-engineering scaffolds, which are porous sponge-like materials that can carry cells and other therapeutics that can slowly degrade or dissolve as it stimulates tissue formation. One problem with the use of tissue engineering scaffolds is that as the tissue grows within the scaffold, it reaches a point where it does not have enough oxygen supply to sustain growth before the tissue is adequately formed.

Several methods for oxygen generation for medical purposes have been described, but all with limitations. One study used angiogenic growth factors to promote vascularization in engineered tissue. However, the results did not indicate a faster rate of circulatory vessel growth; therefore, tissues were still limited in thickness (1: Smith et al., 2004). Another approach uses either dissolved oxygen in a topical cream, or glucose oxidase to capture and transport oxygen from the atmosphere to promote wound healing (4a: Davis, 2007). This approach was reported to only be able to deliver oxygen through about 600 microns of epidermis and dermis (4b,c: Roe, Berg et al, 2012; Roe, Ladininski et al, 2012), and is also limited to topical applications (4d: Roe, Gibbins et al., 2012).

A third approach utilizes decomposition of various inorganic peroxide compounds to generate oxygen. One makes use of calcium peroxide in a scaffold of paraffin (2: Oh et. al, 2008, p. 758). Similarly, Harrison et al. (8: Harrison et al, 2007) reported sodium percarbonate incorporated in films of Poly(d,l-lactide-co-glycolide) (PLGA) for in situ production of oxygen over a period of 24 h. When in contact with ischemic tissue, PLGA/percarbonate decreased tissue necrosis and cellular apoptosis in a mouse model. Still another system uses H2O2 microencapsulated in a PLGA shell that is embedded in an alginate matrix containing immobilized catalase to accelerate H2O2 decomposition to generate 02. This system was shown to provide an environment adequate for cells under a hypoxic environment and to increase cell survival (9: Abdi et al., 2011).

A fourth report investigated unicellular alga *Chlorella* as a natural photosynthetic oxygen generator (12: Bloch et al., 2006).

All of these approaches offer means of oxygen generation that can be used either internally or externally, but do not provide a means of recharging the oxygen reservoir. None of these approaches report the generation of singlet oxygen.

There remains a need for additional compositions and methods for supplying oxygenating materials for the treatment of wounds and the like.

SUMMARY

In contrast to earlier efforts, the approach reported here uses thermal decomposition of organic endoperoxide compounds to produce singlet oxygen.

Certain embodiments include materials that carry oxygen and emit molecular oxygen upon heating (thermo lytic material or compound). In certain aspects the oxygen carrier comprises an organic compound either alone or contained in a polymeric carrier or other carrier material that is used to form a coating, layer, or bulk substance that can be a solid, a gel or a fluid. The oxygen-carrier is most conveniently prepared by oxidation of a precursor compound, the structure of which determines its thermal stability and thus how rapidly oxygen is released at any given temperature.

Certain embodiments are directed to products and devices such as bandages and other wound coverings. In certain aspects the oxygen generating capacity of these devices can accelerate healing (i) by promoting tissue repair and/or (ii) by inhibiting anaerobic infective organisms. Certain aspects are directed to sub-gingival devices for inhibiting gram-negative, facultative periodontal infections, peri-implantitis, and persistent periapical infections. In further aspects an oxygen-emitting tissue-engineering scaffold can be used to facilitate tissue regrowth.

In certain embodiments a material is designed that carries oxygen and emits a highly reactive form of molecular oxygen upon heating. The oxygen carrier consists of an organic endoperoxide compound (thermolytic endoperoxide) either alone or contained in a polymeric carrier or other carrier material. In certain aspects the carrier is a solid, a gel or a fluid. The highly reactive form of $O_2$ is known as "singlet oxygen," "singlet $O_2$," or "$^1O_2$". Singlet oxygen has a very short lifetime and rapidly decays to form ordinary molecular oxygen, $O_2$ (more properly known as "triplet oxygen," "triplet-$O_2$" or "$^3O_2$," and is referred to herein as either "$O_2$" or "oxygen"). $^1O_2$ is well known for its therapeutic use in a variety of medical treatments ranging from cancer to viral, fungal, and bacterial infections; in certain selected circumstances this invention can be extended to include the combined use of both $^1O_2$ and $^3O_2$ therapies. An oxygen generating material may also contain a singlet-oxygen quenching component to accelerate the conversion of $^1O_2$ to $^3O_2$.

An endoperoxide oxygen-carrier (thermolytic endoperoxide) is most conveniently prepared by photo-oxidation of a precursor aromatic organic compound. The precursor aromatic compound can be a fused ring aromatic or a methyl substituted aromatic compound. In certain aspects the aromatic organic compound is dimethyl, trimethyl, or tetramethyl substituted aromatic. Methyl substituted aromatics can comprise an ortho, meta, or para substituted methyl groups. The aromatic organic compound can be a polycyclic aromatic compound or otherwise comprise at least two fused aromatic rings. The structure of the endoperoxide-forming compound determines its thermal stability and thus how rapidly oxygen is released and the precursor compound reformed at any given temperature. By combining two or more endoperoxide compounds, one with a relatively slow release rate at the working temperature, and 1, 2, 3 or more with faster release rates, it is possible to form delivery systems with a wide range of rates, durations, and profiles of oxygen generation to suit a variety of end-use applications. In some applications it is possible to design a system that could be recharged by photo-oxidizing the reformed precursor compound(s).

In certain embodiments an oxygen generating material can be (i) incorporated in to sub-gingival devices for inhibiting microbial growth, (ii) used to treat or inhibit facultative periodontal infections, (iii) to treat peri-implantitis, (iv) to treat persistent periapical infections, and/or (v) facilitate tissue growth.

In certain aspects singlet oxygen is provided as an intermediate species for delivery of triplet (normal) oxygen. Thermal decomposition of organic endoperoxide compounds produce singlet oxygen, which is further transformed into oxygen.

In certain aspect an oxygen generating biomaterial can comprise a fast release thermolytic endoperoxide, a slow release thermolytic endoperoxide, or a slow release thermolytic endoperoxide and a fast release endoperoxide. A biomaterial can further comprise a singlet oxygen quencher. In certain aspect the slow to fast release thermolytic peroxide is present in a ratio of 100:1, 90:1, 80:1, 70:1, 60:1, 50:1, 40:1, 30:1, 20:1, 10:1, 5:1, 2:1, 1:1, 1:2, 1:5, 1:10, 1:20, 1:30, 1:40, 1:50, 1:60, 1:70, 1:80, 1:90, 1:100 of slow release thermolytic endoperoxide to fast release thermolytic endoperoxide, or any ratio there between. In a further aspect the slow release thermolytic endoperoxide can be present as 0.001, 0.01, 0.1, 1, 2, 3, 4, 5, 6, 7, 8, 9, 10, 20, 30, 40, 50 weight percent of the biomaterial, including all values and ranges there between. In a still further aspect the fast release thermolytic endoperoxide can be present as 0.001, 0.01, 0.1, 1, 2, 3, 4, 5, 6, 7, 8, 9, 10, 20, 30, 40, 50 weight percent of the biomaterial, including all values and ranges there between. In certain aspects the singlet oxygen quencher can be present as 0.001, 0.01, 0.1, 1, 2, 3, 4, 5, 6, 7, 8, 9, 10, 20, 30, 40, 50 weight percent of the biomaterial, including all values and ranges there between. In certain aspects the endoperoxide ($ti_{1/2}$ in hours as measured in the presence of $CDCL_3$ at 25° C.) can include 1,4-dimethylnaphthalene-1,4-endoperoxide (5); 1,8-dimethylnaphthalene-1,4-endoperoxide (30); 1,2,4-trimethylnaphthalene-1,4-endoperoxide (70); 1,4,5-trimethylnaphthalene-1,4-endoperoxide (290); 1,2,3,4-tetramethylnaphthalene-1,4-endoperoxide (indeterminant). In other aspects the slow release endoperoxide can include rubrene endoperoxide. In certain aspects a singlet oxygen quencher is beta-carotene or 1,3-diphenylisobenzofuran (DPBF).

Certain embodiments are directed to oxygen-saturated hydrogels (polymeric composition containing at least 20, 30, 40, 50, or 60% water) comprising thermolytic endoperoxides as described herein. Hydrogels are three-dimensional networks of hydrophilic compounds, usually polymers, which have the ability to imbibe a large quantity of water and biological fluids. The network may be formed through either chemical crosslinking (covalent, ionic) or physical crosslinking (entanglements, crystallites, hydrogen bonds). Typically, hydrogels are three-dimensional structures capable of comprising at least 20 wt % water in relation to the weight of the gel. In certain aspects a hydrogel can comprise a polyacrylic acid, sodium polyacrylate, partially neutralized polyacrylate, polyacrylic acid starch, hydroxypropylcellulose, hydroxypropylmethylcellulose, hydroxyethylcellulose, methylcellulose, carmellose sodium, carboxyvinyl polymers and N-vinylacetamide copolymers; these can be used singly or in combination of two or more. The hydrogel can comprise 20, 30, 40, 50, 60 to 40, 50, 60, 70, 80 weight percent of polymer(s). In certain aspects the hydrogels can comprise immobilized perfluorocarbons, such as fluorinated methacrylamide (MACF) chitosan hydrogels (Wijekoon et al. Acta Biomaterialia (2013) 5653-64). The release profile of a fluorinated biomaterial comprising one or more thermolytic endoperoxides can be engineered to provide a variety of oxygen release profiles. In certain aspects a thermolytic endoperoxide can be present as 0.001, 0.01, 0.1, 1, 2, 3, 4, 5, 6, 7, 8, 9, 10, 20, 30, 40, 50 weight percent of the hydrogel, including all values and ranges there between.

As used herein "Treat" refers to any type of treatment that imparts a benefit to a patient, e.g., a patient who is injured or who is afflicted with or at risk for developing a disease (e.g., stroke, myocardial disease, cardiovascular disease, etc.). Treating includes actions taken and actions refrained from being taken for the purpose of improving the condition of the patient (e.g., the relief of one or more symptoms), delay in the onset or progression of the disease, etc. Also, in some embodiments, treating comprises inhibiting, reducing, and/or preventing the disease or symptoms thereof in a subject in need.

As used herein, a "biocompatible" material is a synthetic or natural material used to replace part of a living system or to function in intimate contact with living tissue. Biocompatible materials are intended to interface with biological systems to evaluate, treat, augment or replace any tissue, organ or of the body. The biocompatible material has the ability to perform with an appropriate host response in a specific application and does not have toxic or injurious effects on biological systems. Non-limiting examples of biocompatible materials include a biocompatible ceramic, a biocompatible polymer or a biocompatible hydrogel.

As used herein, "biodegradable" means that the material, once implanted into a host, will begin to degrade.

As used herein, "polymer" means a chemical compound or mixture of compounds formed by polymerization and including repeating structural units. Polymers may be constructed in multiple forms and compositions or combinations of compositions and may be degradable or nondegradable.

As used herein, "biomimetic" shall mean a resemblance of a synthesized material to a substance that occurs naturally in a human body and which is not substantially rejected by (e.g., does not cause an unacceptable adverse reaction in) the human body. When used in connection with the tissue scaffolds, biomimetic means that the scaffold is substantially biologically inert (i.e., will not cause an unacceptable immune response/rejection) and is designed to resemble a structure (e.g., soft tissue anatomy) that occurs naturally in a mammalian, e.g., human, body and that promotes healing when implanted into the body.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
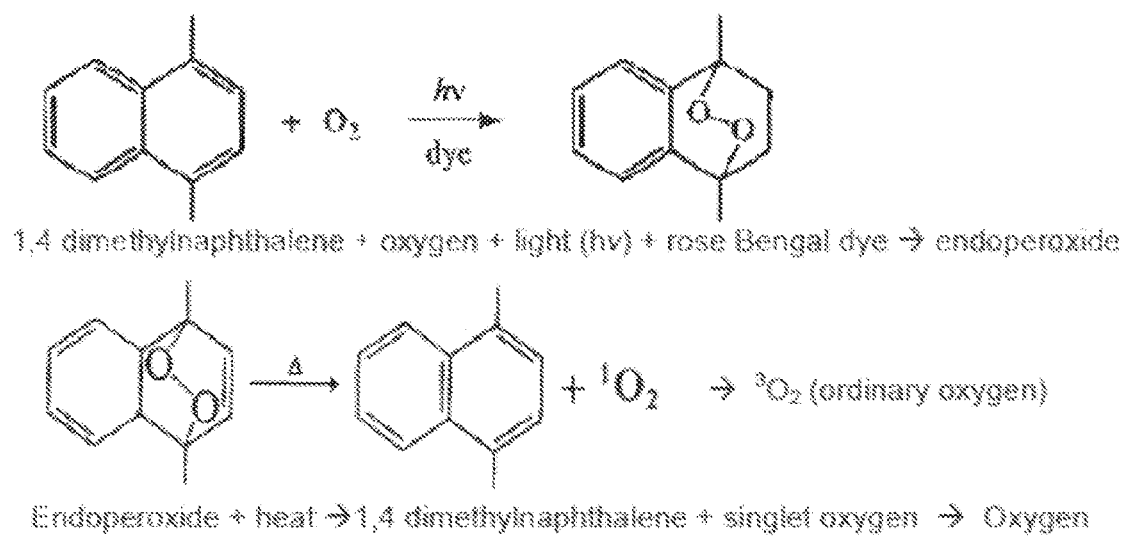
FIG. 1. Method for formation of an endoperoxide for storing oxygen, and means of controlled oxygen release by heat.

Oxygen is important for cell metabolism, especially energy production by means of ATP, and is critical for nearly all wound-healing processes. It prevents wounds from infection, induces angiogenesis, increases keratinocyte differentiation, migration, and re-epithelialization, enhances fibroblast proliferation and collagen synthesis, and promotes wound contraction (Bishop, 2008; Rodriguez et al, 2008). In addition, the level of superoxide production (a key factor for oxidative killing pathogens) by polymorphonuclear leukocytes is critically dependent on oxygen levels.

Due to vascular disruption and high oxygen consumption by metabolically active cells, the microenvironment of the early wound is depleted of oxygen and is hypoxic. Several systemic conditions, including advancing age and diabetes, can create impaired vascular flow, thus setting the stage for poor tissue oxygenation. In the context of healing, poor perfusion creates a hypoxic wound. Chronic wounds are notably hypoxic; tissue oxygen tensions have been measured transcutaneously in chronic wounds from 5 to 20 mm Hg, in contrast to control tissue values of 30 to 50 mm Hg (Tandara and Mustoe, 2004).

In wounds where oxygenation is not restored, healing is impaired. Temporary hypoxia after injury triggers wound healing, but prolonged or chronic hypoxia delays healing (Bishop, 2008; Rodriguez et al, 2008). In acute wounds, hypoxia serves as a signal that stimulates many aspects of the wound-healing process. Hypoxia can induce cytokine and growth factor production from macrophages, keratinocytes, and fibroblasts. Cytokines that are produced in response to hypoxia include PDGF, TGF-β, VEGF, tumor necrosis factor-a (TNF-a), and endothelin-1, and are crucial promoters of cell proliferation, migration and chemotaxis, and angiogenesis in wound healing (Rodriguez et al, 2008).

In normally healing wounds, reactive oxygen species (ROS) such as hydrogen peroxide and superoxide are thought to act as cellular messengers to stimulate key processes associated with wound healing, including cell motility, cytokine action (including PDGF signal transduction), and angiogenesis. Both hypoxia and hyperoxia increase ROS production, but an increased level of ROS transcends the beneficial effect and causes additional tissue damage (Rodriguez et al, 2008).

Thus, oxygen is crucial for wound healing. Hypoxia stimulates wound healing such as the release of growth factors and angiogenesis, while oxygen is needed to sustain the healing process (Bishop, 2008). One therapeutic option that can sometimes overcome the influence of tissue hypoxia is hyperbaric oxygen therapy (HBOT; Rodriguez et al, 2008). While HBOT can be an effective treatment for hypoxic wounds, its availability is limited.

Certain embodiments are directed to making and using oxygen-generating biomaterials to assist in the growth of new tissues. New tissues can be grown using tissue engineering, which is a technique that uses materials or processes to replace or repair tissues, using for example tissue scaffolds. Scaffolds are three-dimensional structures that can mimic the "in vivo" environment and facilitate cell growth. Certain aspects of the methods and compositions described herein provide new methods and materials to nourish and promote new tissue by generating oxygen to support tissue regeneration and growth.

I. Thermolytic Compounds

Thermolytic compounds as used herein are endoperoxide compounds that generate singlet oxygen at a temperature of about or at least 20, 25, 30, 35, 40, 45, 50° C. or higher, including all values and ranges there between. The $ti/_2$ half-life is temperature dependent. This aids in both storage and release. The $ti/_2$ is longer the lower the storage temperatures. The half-life is also dependent on structural features and can be selected individually or in combinations to tailor and adjust the $^1O_2$ generation profile (and hence the $^3O_2$ generation profile) to suite a wide range of end-use applications.

Endoperoxides are organic ring molecules (aromatics) that release singlet oxygen when exposed to sufficient heat (3 a; 3b). The oxygen is stored covalently within the carbon ring structure of the molecule. Photooxidation is the process used to store oxygen as endoperoxides and takes place in the presence of oxygen, a photosensitizer and intense light (3; 5). Endoperoxides decompose thermally to liberate oxygen at varying rates, depending on their molecular structure. The thermal decomposition and release is often expressed by a half-life. If several endoperoxide compounds decay at different rates when exposed to body heat, a calculated concentration of each particular compound can be developed to release oxygen at differing rates at different time periods. This would be useful in several scenarios—such as in mirroring the wound healing process to provide the right amount of oxygen at a given moment in time or stage of healing (3 a; 3b). An oxygen-generating scaffold with these capabilities can overcome the perfusion obstacle in tissue engineering and allow a huge increase in the healing power of artificial bio films.

The endoperoxide oxygen-carrier is most conveniently prepared by photo-oxidation of a precursor aromatic organic compound. The structure of the endoperoxide-forming compound determines its thermal stability and thus how rapidly oxygen is released and precursor compound reformed (via a "retro-Diels-Alder reaction") at any given temperature. At body temperature the half-life ($ti/_2$) for thermal release of $^1O_2$ from an endoperoxide (also known as "thermolysis") can range from seconds to days. By combining two or more endoperoxide compounds, one with a relatively slow release rate (long $ti/_2$) at the working temperature, and one or more with faster release rates (short $ti/_2$), it is possible to form delivery systems with a wide range of rates, durations, and profiles of oxygen generation to suit a variety of end-use applications. In some applications it is possible to design a system that could be recharged by photo-oxidizing the reformed precursor compound(s). FIG. 1 illustrates an example of the chemistry involved.

In certain aspects 1,4 dimethylnaphthalene (Formula I) and/or rubrene (Formula II) are used as precursors to generate endoperioxde derivatives that degrade under heat to singlet oxygen. Rubrene (5,6,11,12-tetraphenylnaphthacene) is a red colored polycyclic aromatic hydrocarbon that is used as a sensitiser in chemo luminescence. Endoperoxides are heterocycles that contain a peroxide group (—O—O—) in the ring of the heterocycle.

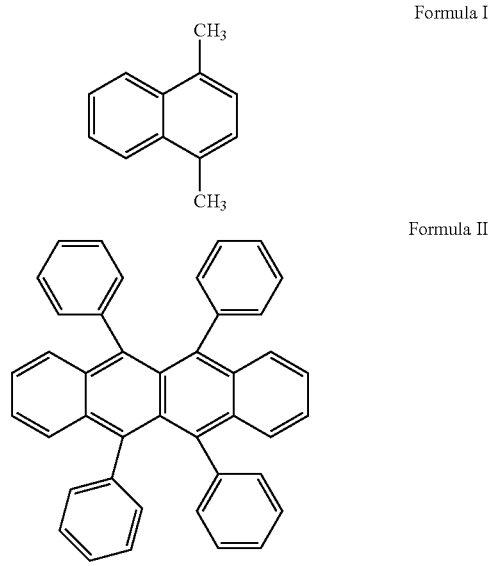

Studies were performed to confirm singlet oxygen generation from rubrene endoperoxide. Materials include 1,4 dimethylnaphthalene; Rose Bengal, electric analytical balance; manual glass pipettes; Low-actinic storage bottles; sodium chloride plates; red-light lamp; 200 ml glass beaker; FT-IR spectrometer (linked to a computer installed with OMNIC); white-light lamp; ice packs; Refrigerator; and Vacuum oven.

In one method a Rubrene, Acetone, and Polystyrene film was placed inside a cuvette. A spectrophotometer was used to detect oxygen levels in the cuvette.

In a further method no spectrophotometer was used and a Rubrene, Acetone, and Polystyrene film was created in Petri dish, and observe physically for oxygen formation.

In still a further method a Rubrene and High Gel 4442 gel with Rubrene was created, and observe physically for oxygen formation.

In another method Rubrene and liquid styrene gel was formed and observe physically for oxygen formation.

The studies supported the use of endoperoxide compounds as oxygen-generating biomaterials.

Additional studies were performed to provide indirect measures of oxygen storage and recovery—Absorption spectra of the endoperoxide forming compound and its reversal to reform the original compound. 0.002 g Rubrene and 0.029 g Aquazol 50 polymer were dissolved in 15 mL 2-propanol (4 mm cuvette). The 0.002 g Rubrene and 0.029 g Aquazol 50 in 12 mL 2-propanol was exposed to light for 30 minutes while in an ice water bath (4 mm cuvette). After light exposure the composition was heated: 0.002 g Rubrene and 0.029 g Aquazol 50 in 15 mL 2-propanol after 30 min in light oven while in an ice water bath and 2 hrs (120 min) in a 70° C. water bath (4 mm cuvette).

Figure 2:
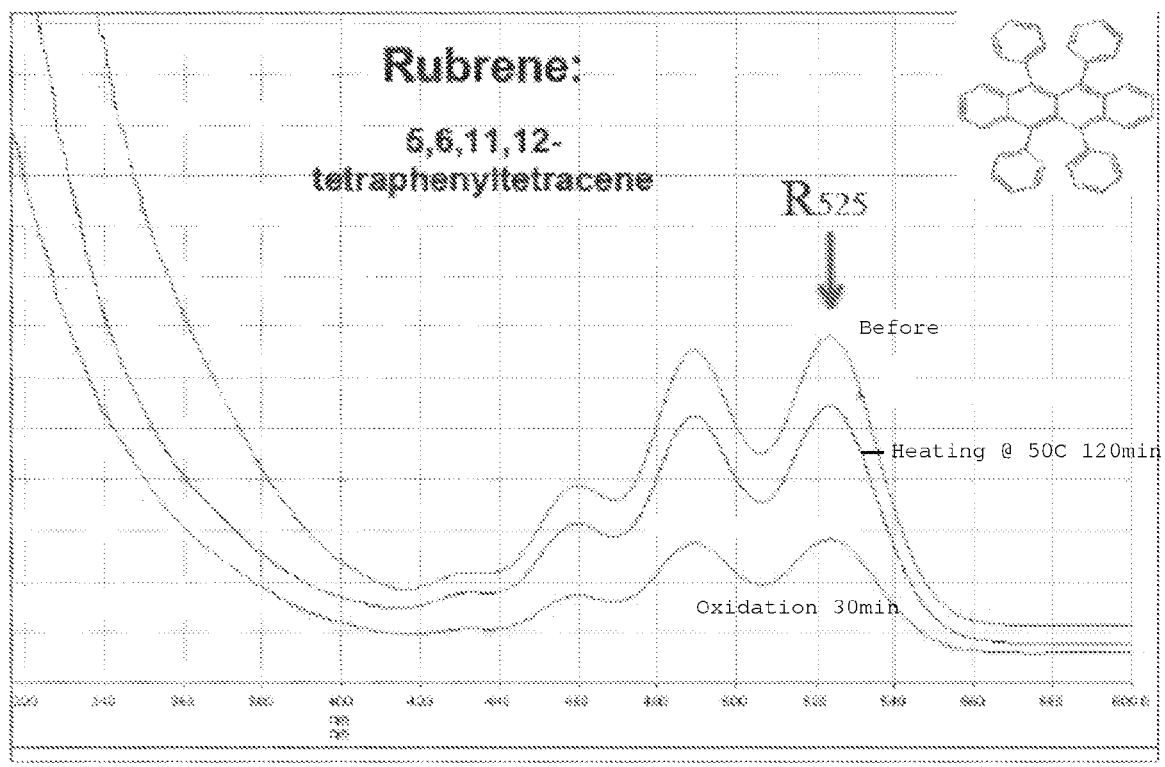
FIG. 2. Formation of rubrene endoperoxide in about 67% yield, by photo-oxidation, followed by recovery of about 75% of the original rubrene, or about 55% of the rubrene converted to endoperoxide, as a result of heating at 50° C. for 120 minutes.
Figure 3:
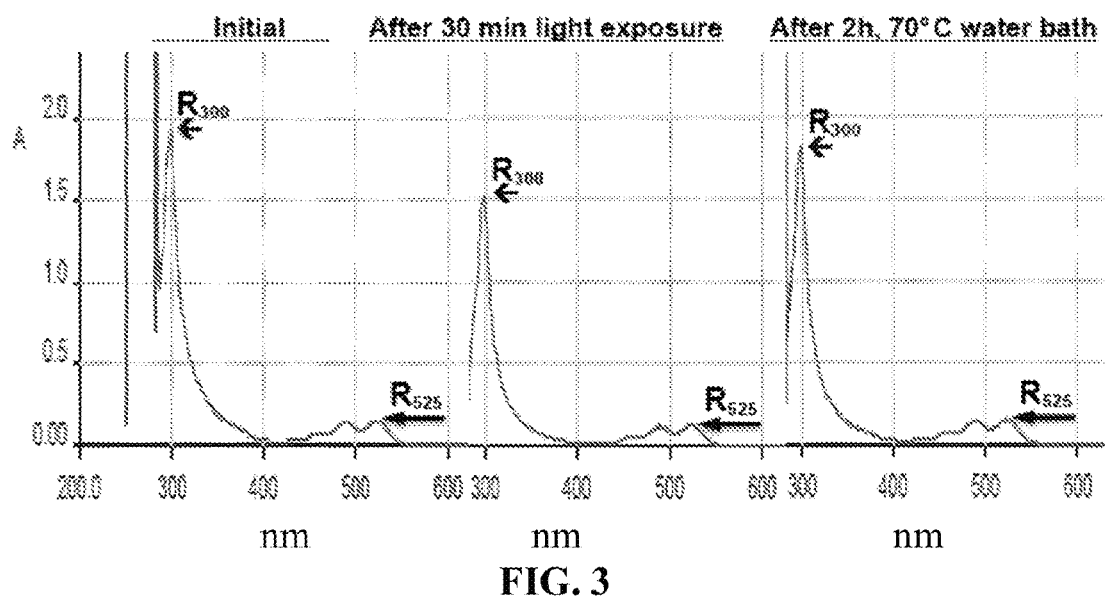
FIG. 3. Similar results as FIG. 2, but also showing the short wavelength band of rubrene at 300 nm 0.002 g Rubrene in 0.029 g Aquazol 50 polymer. Spectra taken of solution in 15 mL of 2-propanol in 4 mm path length cuvette.
Figure 4:
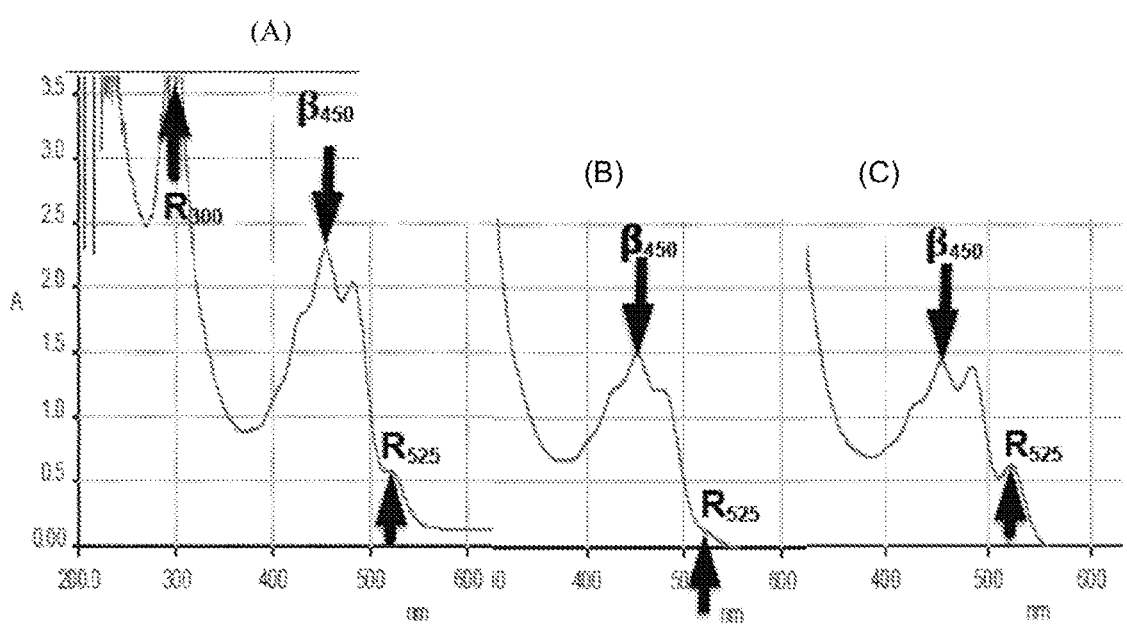
FIG. 4. Endoperoxide formation in presence of betacarotene, a strong singlet-02 quencher. (A) Solution of 0.004 g rubrene and 0.0015 g beta-carotene in 24 mL isopropanol. Combination spectra of beta-carotene and rubrene in isopropanol solution. The betacarotene peak and rubrene peak near 490 nm add together at about 450 nm to create a spectrum with higher absorbance at all wavelengths, except for the rubrene band at about 525 nm, which does not overlap with the beta-carotene spectrum. (B) Post-photooxidation state, liquid solution: 0.004 g rubrene and 0.0015 g betacarotene per 24 mL isopropanol. (C) 6 Post-thermal exposure, 1 hour at 50° C., liquid solution: 0.004 g rubrene and 0.0015 g betacarotene per 24 mL isopropanol.

After exposure to light, FIG. 4B, the rubrene spectrum disappears, as observed by the lack of a rubrene peak at about 525 nm. This is evidence for the conversion of the rubrene solute into an endoperoxide with oxygen stored in its carbon structure. In FIG. 4C, after heating in a water bath for 1 hour at 50° C., the 525 nm rubrene peak returns. Rubrene appears to have been fully converted, and to have been fully recovered by heating, in contrast to FIG. 2, without the presence of beta-carotene. This is evidence that the endoperoxide has released oxygen and reformed rubrene, and that in the presence of the singlet oxygen inhibitor beta-carotene, the "round trip" is more efficient. Note, however, that compared to FIG. 4A, a decrease is also seen in the levels of beta-carotene from an absorbance of about 2.25 to about 1.5 at the beta-carotene peak at 450 nm after heating. Thus, the beta-carotene appears to have been partially sacrificed in the process.

Additional studies were perform that directly measure oxygen storage and recovery—two types of $O_2$-sensing probes were used. Two methods for direct detection of oxygen release via thermolysis of an endoperoxide were utilized.

Figure 5:
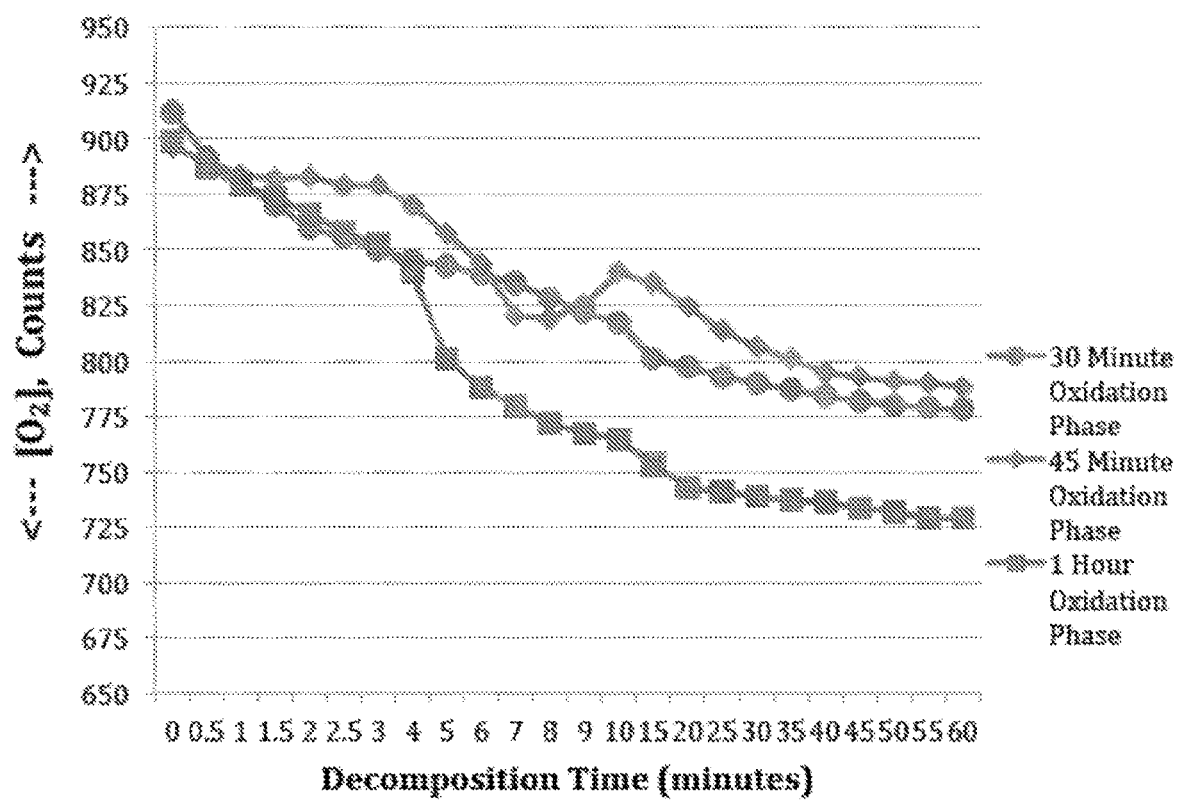
FIG. 5. Oxygen release from 75° C. decomposition of rubrene endoperoxide. Oxygen release from rubrene endoperoxide, as measured directly with a fluorescent oxygen probe. Each point is the average of 5 (n=5).
Figure 6:
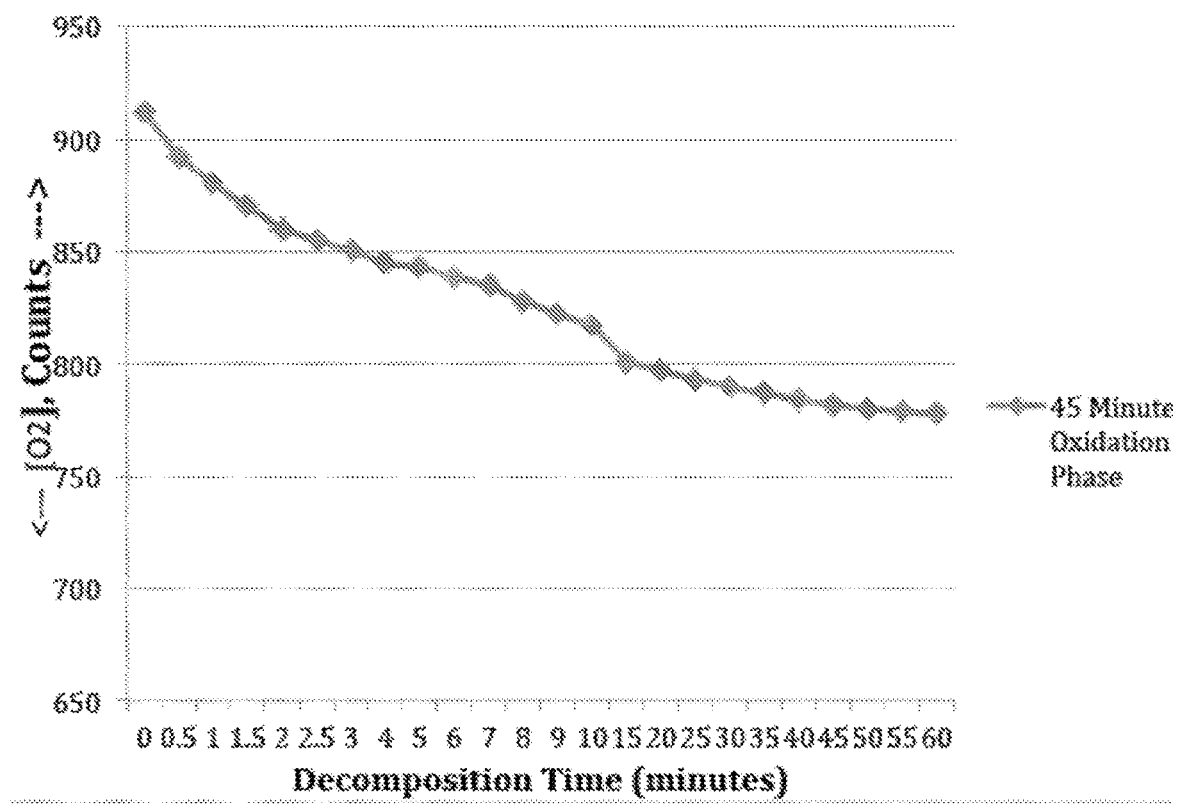
FIG. 6. Oxygen release from 75° C. decomposition of dimethyl naphthalene endoperoxide. Represents the release of oxygen from dimethyl naphthalene endoperoxide at 75° C., serving in place of rubrene endoperoxide. Specimens per sample=5 (n=5).

The first direct measure of oxygen used a fiber optic with a fluorescent probe. The optical fiber carries excitation light produced by a blue LED to a coating at the probe tip. Fluorescence generated at the tip is collected by the probe and carried by the optical fiber for measurement by a portable fluorometer. When oxygen diffuses into the thin-film coating, it quenches (suppresses) the fluorescence. The degree of quenching correlates to the level of oxygen pressure/concentration in the environment surrounding the probe. Thus, as $O_2$ concentration increases, the fluorescent signal decreases. FIG. 5 and FIG. 6 show that the longer the photooxidation exposure, the more $O_2$ is produced.

The quenching effect here is less on average than with Rubrene that was oxidized for the same period of time. The reason being that the di-methyl naphthalene is present in a much greater molar amount compared to rubrene and so would give off oxygen in a much higher concentration in a shorter period of time.

The second direct measure of oxygen used an electrochemical cell. This method employs a Vernier LabQuest O2 Gas Sensor™ to measure oxygen concentration in the 0 to 27% range, by means of an electrochemical cell. The cell contains a lead anode and a gold cathode immersed in an electrolyte. Oxygen molecules entering the cell are electrochemically reduced at the gold cathode and generates a current that is proportional to the oxygen concentration.

Figure 7:
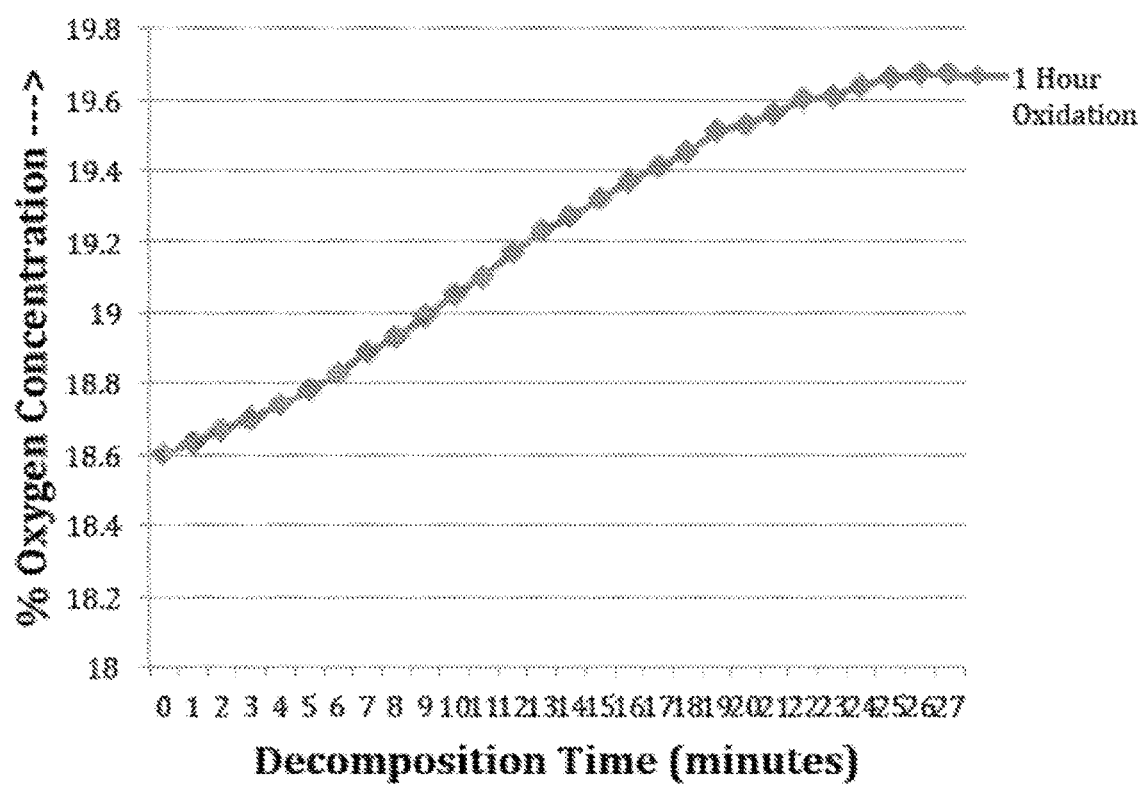
FIG. 7. Affect of rubrene decomposition at 75° C. on oxygen release (% 02 Concentration). Oxygen release from rubrene endoperoxide, as measured directly with an electrochemical oxygen probe (Vernier 02 Gas Sensor), (n=1).

FIG. 7 shows the results of rubrene endoperoxide decomposition at 75° C. on oxygen release. Note that, in contrast to FIG. 5 and FIG. 6, $O_2$ Concentration is shown increasing upward due to the alternative analytical method used.

II. Oxygen Generating Biomaterials

A. Wound Dressing

Compositions described herein can be incorporated into wound dressings. In certain aspects wound dressings include those dressings used in aseptic techniques, such as wound care, peripheral IV catheter insertion and care, or the like. Other embodiments include field dressings of the type found in a military first aid case, and adhesive plastic and fabric film bandages, e.g., Band-Aid™-type bandages.

The wound dressing material can include, but is not limited to a hydrocolloid, a hydrogel, a semi-permeable transparent film, an open-cell foam, an alginate, an absorptive filler, a woven fabric and a non-woven fabric or a combination of such materials.

The selection of a particular wound dressing is normally made on the basis of functionality (absorption of wound exudates, control of bleeding or fluid loss, maintenance of moist wound surface and protection against contamination, desiccation and abrasion), wound size and avoidance of trauma upon removal from the wound site.

Hydrocolloidal wound dressing material typically comprises an absorbent and elastomer combined to form an adhesive base. Carboxymethylcellulose is commonly used as the absorbent component. Some hydrocolloid dressings contain pectin. These dressings are moisture retentive and promote autolytic debriding. They are also highly occlusive, providing protection against exogenous contaminants. They are available in wafer form in a variety of shapes, as well as granules, powders, and paste. Representative examples of dressings of this type include Comfeel, Duo Derm and Repli Care. See also, U.S. Pat. Nos. 6,033,684, 4,551,490 and 4,393,080. Hydrocolloid dressings may be secured to a wound site by means of a transparent film cover that is impermeable to liquid, bacteria and viruses. Alternatively, the hydrocolloid wound dressing material may be laminated to a backing film.

In accordance with the above-cited U.S. Pat. No. 4,551,490, the wound dressing of the present invention may be produced from at least one finely divided or granular, water-soluble and/or water-swellable absorbent material dispersed in a pressure-sensitive, synthetic or natural elastomeric binder, which forms an adhesive composition. A layer of the adhesive composition is disposed on a thin, pliable, water-insoluble support film or carrier to yield the finished product.

Suitable absorbent materials include, but are not limited to sodium carboxymethylcellulose, pectin, gelatin and the like.

Representative examples of elastomeric binders include, without limitation, at least one of polyisobutylene, isobutylene copolymers (e.g., butyl rubber), polyisoprene, nitrile rubber (NBR) and, optionally, styrene-containing copolymers, e.g., styrene-butadine rubber.

The wound dressing can include a tackifier. Typical tackifiers include modified rosin, e.g., modified tall coil rosin (UNI-T AC® 70resin—Arizona Chemical), modified rosin in mineral spirit solution (UNI-TAC® 72—Arizona Chemical), beta-pinene (SYLVARES® TR B115—Arizona Chemical), rosin esters, e.g., pentaerythritol esters of rosin (PENTALYN® H—Pinova) and glycerol ester of partially hydrogenated rosin (STAYBALITE® ester 10—Pinova).

Other optional components of the wound dressing can include one or more of a plasticizer or solvent, such as mineral oil or petrolatum; an antioxidant such as the IRGANOX® (BASF) series of high molecular weight stabilizers for organic substrates; a deodorant or a fragrance.

A hydrogel can be described generally as an insoluble polymer with hydrophilic sites which absorb and interact with significant volumes of liquid, particularly water or in the case of wound dressings, wound exudates. A hydrogel-based wound dressing material typically comprises cross-linked hydrophilic macromolecules containing up to about 95% water by weight. These dressings are effective for establishing and maintaining a moist microenvironment for cell migration and rehydrating eschar and slough for easy removal from the wound. They also diminish wound pain. Representative examples of hydrogel dressings include, without limitation, Solo Site, Intra Site and Carrasyn Gel. See also, U.S. Pat. Nos. 6,238,691, 5,112,618, 5,106,629 and 4,909,244. The hydrogel material may be in sheet or gel form, and in the latter case can be applied directly to the wound, or impregnated in an absorbent compress, e.g., gauze, which is used for dressing the wound. The absorbent compress may be bound to the wound by a suitable bandage material.

Alginate wound dressings comprise non-woven fibers of soluble salts of alginic acid, a derivative of seaweed. These dressings are moisture-retentive, non-occlusive and non-adherent, and are capable of absorbing moderate to heavy wound exudates in superficial and deep wounds. They are available in pad (felt) and rope form, the latter being useful as a filler for deep or tunneling wounds. Representative examples of such dressings include, without limitation, Kaltostat™ and Curasorb®. See also U.S. Pat. Nos. 5,836,970; 5,197,945; 4,948,575; and U.S. Publication No. 2005/0287193.

In another embodiment, the wound dressing may be in the form of a bandage strip and an absorbent compress attached to the bandage strip. This form of dressing is commonly referred to as a first aid field dressing. Preferably, the absorbent compress is gauze, e.g., cotton or chemical derivative of cellulose, or an open cell foam material (e.g., hydrophilic polyurethane foam, optionally gel film or silicon coated). A wound dressing of this type may be applied as a dry dressing or a water dressing, i.e., a dressing that is kept wet with sterilized water or saline solution. It is conventionally packaged in an air-tight container.

The wound dressing may also be embodied in an adhesive bandage comprising a flexible substrate coated with a pressure-sensitive adhesive coating and an absorbent compress affixed to at least part of the adhesive coated substrate, with the absorbent compress having incorporated therein one or more of the compositions described herein. The flexible substrate may be a plastic or fabric film, which is in the form of a strip, a patch or a spot.

In addition to their utility in wound dressings, the above-described compositions can be used to enhance the efficacy of topical wound treatment preparations, such as ointments, creams, gels, lotions, emulsions, pastes, liniments and collodions. For example, the improvement can be realized by incorporating into standard liniment or collodion preparations an effective amount of the compositions described herein.

B. Tissue Scaffolds

Certain embodiments are directed to tissue scaffolds engineered to generate oxygen. Tissue scaffolds can include an acellular tissue matrix (ATM) that has the biologic ability to support tissue regeneration. In some embodiments, tissue scaffolds can support cell ingrowth and differentiation. For example, the scaffolds can be used for tissue ingrowth, orthopedic surgery, periodontal applications, tissue remodeling, or tissue restoration. In one embodiment, the tissue scaffolds produce a regenerative tissue response, as demonstrated by the presence of fibroblast-like cells and blood vessels.

In certain aspects, tissue scaffolds can include one or more polymeric materials, which can be selected from a number of polymer types. As used herein, the polymeric materials can include synthetic polymers and/or naturally occurring polymers. Furthermore, the polymeric materials can include individual polymers and/or polymer blends, and/or copolymers (polymers with two or more monomer repeating units in their chains). In some embodiments, the polymeric materials can include polyglycolide, polylactide, polydioxane (or other polyether esters), poly(lactide-co-glycolide) (PLG), and/or polyhydroxyalkonates. For example, in certain embodiments, the polymeric material can include polyhydroxyalkonates such as, for example, polyhydroxybutyrate (e.g., poly-3-hydroxybutyrate, poly-4-hydroxybutyrate (P4HB)), polyhydroxy valerate, polyhydroxyhexanoate, polyhydroxyoctanoate, or trimethylene carbonate.

In various embodiments, tissue scaffolds disclosed herein can be used to treat any of a wide range of disorders. Tissue defects can arise from many causes, including, for example, congenital malformations, traumatic injuries, infections, and oncologic resections. The tissue scaffolds can be used to treat musculoskeletal defects, e.g., as an articular graft to support cartilage regeneration. The tissue scaffolds can also be used to treat defects in any soft tissue, e.g., tissues that connect, support, or surround other structures and organs of the body. Soft tissue can be any non-osseous tissue.

The tissue scaffolds can be used to treat soft tissues in many different organ systems. These organ systems can include, but are not limited to, the muscular system, the genitourinary system, the gastroenterological system, the integumentary system, the circulatory system, and the respiratory system. The tissue scaffolds can also be useful to treat connective tissue, including the fascia, a specialized layer that surrounds muscles, bones, and joints of the chest and abdominal wall, and for repair and reinforcement of tissue weaknesses in urological, gynecological, and gastroenterological anatomy. In some embodiments, the tissue or organ in need of treatment can be selected from the group consisting of skin, bone, cartilage, meniscus, dermis, myocardium, periosteum, artery, vein, stomach, small intestine, large intestine, diaphragm, tendon, ligament, neural tissue, striated muscle, smooth muscle, bladder, urethra, ureter, and gingival tissues or organs.

REFERENCES

1. Smith et al, Tissue Engineering 2004; 10:63-71.
2. Oh et al. (2008, Jun. 16). J Biomaterials. 2008.09.065; 757-762.
3(a). Bloodworth and Eggelte, Endoperoxides in Singlet 02; A. A. Frimer, (Ed.), CRC Press: Boca Raton, Fla., 1985; Vol. II, Ch. 4.
3(b). Posavec D (October 2010). Adjustment of the decay kinetics of photogenerated endoperoxides embedded in various carrier materials aiming at medical application. PhD Dissertation, University of Regensburg, Federal Republic of Germany.
4(a). Davis, 2007. How might we achieve oxygen balance in wounds? International Wound Journal, Vol 4 1742-48, 2007.
4(b). Roe et al. (accessed September 2012). An evaluation of a topical dissolved oxygen delivery device on dermal cell viability. Retrieved from AcryMed website: acrymed.com/TDoxygen.html.
4(c). Roe et al. (accessed September 2012). A laboratory evaluation of topical oxygen delivery devices intended to promote healing. Retrieved from Acrymed website: acrymed.com/TDoxygen.html.
4(d). Roe et al. Journal of Surgical Research, March 2010 Volume 159, Issue 1, Pages e29-e36
5. Schaap et al. Polymer-based Sensitizers for photooxidations. II. Journal Of the American Chemical Society, 97(13): 3741-3745.
6. Steinbeck et al. (1992, July). Intracellular Singlet oxygen generation by phagocytosing neutrophils in response to particles coated with a chemical trap. Journal Of Biological Chemistry, 267(19).
7. Galway and Hood. (1979 Mar. 21). Thermal Decomposition Of Sodium Carbonate Perhydrate In Solid State. The Journal Of Physical Chemistry, Vol. 83, 1810-1815.
8. Harrison et al. (2007 Aug. 2). Oxygen Producing Biomaterials For Tissue Regeneration. Biomaterials 28 (31): 4628-4634.
9. Abdi et al. An enzyme-modulated oxygen-producing microsystem for regenerative therapeutics. International Journal of Pharmaceutics. May 2011, Vol. 409, No. 1-2: 203-205.
10. Zhang et al. Oxygen delivery scaffold for tissue engineering. Controlled Release Society, 2012 CRS Annual Meeting Abstracts 11. Bloch et al. Photosynthetic Oxygen Generator for Bioartificial Pancreas, Tissue Engineering 12(2), 2006.
12. Guo and DiPietro. Factors Affecting Wound Healing, J Dent Res 89(3): 2010.
13. Lan Luo. Kinetics of Singlet Oxygen Release from Endoperoxides of 2-Pyridone derivative, Bachelor of Science Dissertation, Worcester Polytechnic Institute, May 3, 2011.
14. Ouchi et al. J. Agric. Food Chem., 201 58:9967-9978.
15. Carlsson et al. Photooxidation of Unsaturated Oils: Effects of Singlet Oxygen Quenchers.
16. Rawls and Santen. A Possible Role for Singlet Oxygen in the Initiation of Fatty Acid Autooxidation.

What is claimed:

1. An oxygen-generating material in the form of a wound covering comprising:
   (a) an absorbent material selected from the group consisting of carboxymethylcellulose, pectin, and gelatin, and
   (b) a rubrene endoperoxide; and
   (c) a singlet oxygen quencher that forms triplet oxygen, wherein the singlet oxygen quencher is beta-carotene or 1,3-diphenylisobenzofuran.

2. An oxygen-generating material in the form of a tissue implant for facilitating growth of new tissues, comprising:
   (a) a polymer selected from the group consisting of polyglycoside, polylactide, polyether esters, poly(lactide-co-glycolide) and polyhydroxyalkonates, and
   (b) a rubrene endoperoxide; and
   (c) a singlet oxygen quencher that forms triplet oxygen, wherein the singlet oxygen quencher is beta-carotene or 1,3-diphenylisobenzofuran.

3. The tissue scaffold of claim 2, wherein the tissue implant is a dental implant.

4. The tissue scaffold of claim 3, wherein the dental implant is a sub-gingival implant.

5. The material of claim 2, further comprising a carrier.

6. The material of claim 5, wherein the carrier is a solid, gel, hydrogel, or semisolid.

* * * * *